United States Patent [19]

Kloepfer

[11] Patent Number: 4,883,764
[45] Date of Patent: Nov. 28, 1989

[54] BLOOD TEST STRIP

[76] Inventor: Mary A. Kloepfer, 10930 Braewick Dr., Carmel, Ind. 46032

[21] Appl. No.: 75,391

[22] Filed: Jul. 20, 1987

[51] Int. Cl.$^4$ ................... G01N 33/48; G01N 31/22
[52] U.S. Cl. ........................... 436/63; 422/56; 422/57; 422/58; 436/177; 436/178
[58] Field of Search ................ 436/63, 162, 161, 170, 436/177, 178; 422/56-58, 61; 435/805, 810; 210/500.24, 500.26, 508, 509, 679

[56] References Cited

U.S. PATENT DOCUMENTS

| | | |
|---|---|---|
| 3,552,928 | 1/1971 | Fetter .................................. 436/177 |
| 3,630,957 | 12/1971 | Rey et al. . |
| 3,663,374 | 5/1972 | Moyer et al. . |
| 3,915,647 | 10/1975 | Wright . |
| 4,108,729 | 8/1978 | Mennen .............................. 422/56 |
| 4,132,650 | 1/1979 | Kirsch et al. . |
| 4,189,304 | 2/1980 | Adams, Jr. et al. . |
| 4,246,107 | 1/1981 | Takenaka et al. . |
| 4,256,693 | 3/1981 | Kondo et al. . |
| 4,288,228 | 9/1981 | Oberhardt .......................... 436/170 |
| 4,312,834 | 1/1982 | Vogel et al. . |
| 4,330,410 | 5/1982 | Takenaka et al. . |
| 4,369,117 | 1/1983 | White . |
| 4,391,906 | 7/1983 | Bauer . |
| 4,442,204 | 4/1984 | Greenquist et al. . |
| 4,446,232 | 5/1984 | Liotta . |
| 4,447,526 | 5/1984 | Rupchock et al. . |
| 4,460,684 | 7/1984 | Bauer . |
| 4,461,829 | 7/1984 | Greenquist . |
| 4,477,575 | 10/1984 | Vogel et al. ....................... 422/57 |
| 4,518,565 | 5/1985 | Boger et al. . |
| 4,532,107 | 7/1985 | Siddigi . |
| 4,543,338 | 9/1985 | Chen . |
| 4,582,684 | 4/1986 | Vogel et al. . |
| 4,587,099 | 5/1986 | Rothe et al. . |
| 4,604,264 | 8/1986 | Rothe et al. ....................... 422/56 |

FOREIGN PATENT DOCUMENTS

| | | |
|---|---|---|
| 0198628 | 10/1986 | European Pat. Off. .............. 422/56 |
| 2150884 | 4/1973 | Fed. Rep. of Germany . |
| 2453813 | 5/1976 | Fed. Rep. of Germany . |
| 2545749 | 5/1976 | Fed. Rep. of Germany . |
| 3523439 | 1/1987 | Fed. Rep. of Germany ...... 436/170 |
| 53-28495 | 3/1978 | Japan . |

OTHER PUBLICATIONS

Walter, "Dry Reagent Chemistries in Clinical Analysis", *Analytical Chemistry*, 55:498 A (1983).

*Primary Examiner*—Michael S. Marcus
*Assistant Examiner*—Rebekah A. Griffith
*Attorney, Agent, or Firm*—E. Victor Indiano

[57] ABSTRACT

A blood test strip includes a support member having an upper surface and lower surface. A separating member is disposed on the upper surface of the support member, and includes an upstream end and a downstream end. A recipient member is disposed on the upper surface of the support member in a side by side relation to the separating member. The recipient member includes an upstream end disposed in an adjacent, non-interwoven relation to the downstream end of the separating member to define an incision therebetween.

25 Claims, 3 Drawing Sheets

U.S. Patent Nov. 28, 1989 Sheet 1 of 3 4,883,764
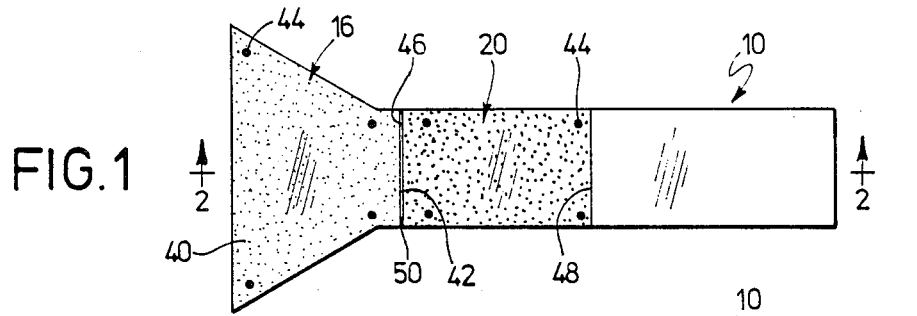
FIG. 1
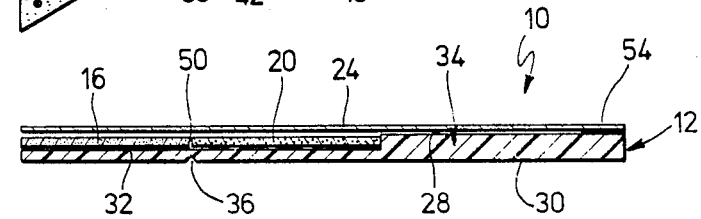
FIG. 2
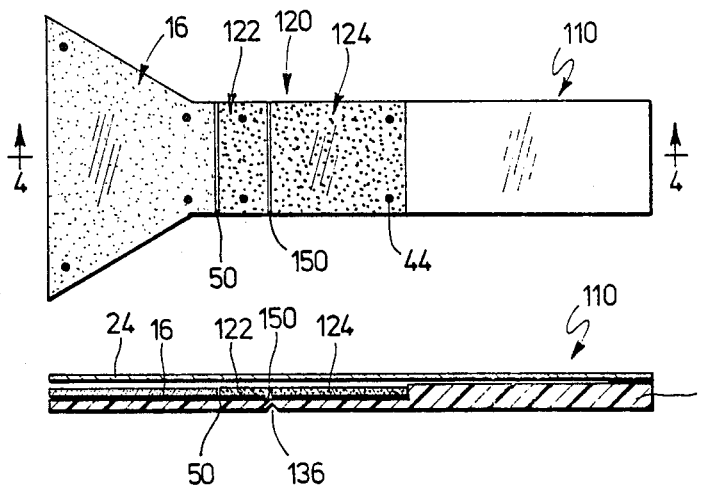
FIG. 3
FIG. 4
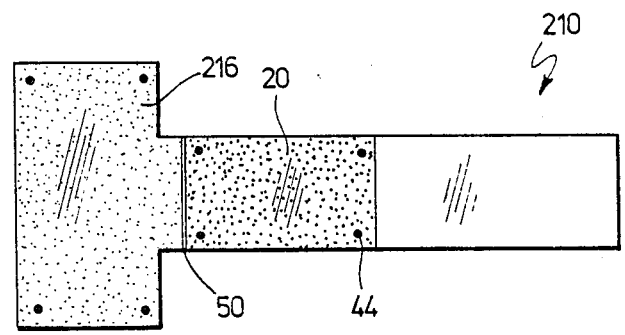
FIG. 5

BLOOD TEST STRIP

BACKGROUND OF THE INVENTION

The present invention relates to methods and devices for the testing of blood constituents, and more particularly to a blood test strip, and a method of using a blood test strip to prepare a blood sample for analysis.

In recent years, there has been a marked increase in the awareness of health issues. One manifestation of this awareness is that an increased importance is being placed on the use of preventive medicine to maintain good health. The widespread adoption of preventative medicine has resulted in an increase in the frequency of the testing for certain conditions, such as abnormal glucose and cholesterol levels, which indicate the existence of a disease, or the propensity to acquire a disease or disorder.

The monitoring and detection of these conditions often is performed by analyzing a patient's blood to determine whether a particular substance exists in the patient's blood, or to determine the amount of that substance in a patient's blood. As a consequence of this increased monitoring, blood tests are being performed on a more frequent basis. Formerly, these tests were usually performed in large hospital or independent laboratories, for only large laboratories performed a sufficient volume of tests to justify the large expenditures often required for sophisticated laboratory equipment.

Recently, however, the trend in blood testing has been to utilize blood tests which can provide a reliable qualitative or quantitative blood analysis without the need to utilize a large, expensive blood analyzing device located in a distant laboratory. To this end, tests have been devised which are suited for use by physicians in their office, and even patients in their homes.

One difficulty encountered in the testing of blood is that it is generally necessary to separate the plasma or serum component of the blood from the cellular components of the blood such as the red and white blood cells, as the presence of these cellular components usually interferes with the test. This problem can be especially acute in photometric or colorimetric reactions wherein the results of the test are often expressed as a color (or particular shade of a color) formed by the reaction of a chemical reagent with a component of the plasma or serum sample. Generally, this separation of the from the cellular components is performed by centrifugation. Recently, however, blood test strips have been designed which can separate the plasma from the cells contained in a blood sample. Examples of such test strips are disclosed in Vogel et. al., U.S. Pat. No. 4,477,575.

However, known blood test strips are generally incapable of collecting a defined volume of plasma and removing that plasma for subjection to chemical analysis. Furthermore, known blood test strips generally require the user to place a precisely measured amount of blood on the test strip.

It is one object of the present invention to provide a simple, yet versatile and easy to use blood test strip for separating the plasma or serum component of a blood sample from the cellular components, and for collecting the plasma or serum so separated in a manner which will enable the sample to be subjected to analysis to detect the presence or the concentration of a particular substance in the blood.

SUMMARY OF THE INVENTION

In accordance with the present invention, a blood test strip is provided which comprises a support member having an upper surface and a lower surface. A separating member is disposed on the upper surface of the support member, and includes an upstream end and a downstream end. A recipient member is disposed on the upper surface of the support member in a side by side relation to the separating member. The recipient member includes an upstream end disposed in an adjacent, non-interwoven relation to the downstream end of the separating member to define an incision therebetween.

Preferably, the support member also includes a detachment means disposed adjacent to the incision for permitting the separating member to be detached from the recipient member.

Also in accordance with the present invention, a method is provided for separating plasma from whole blood. The method includes the step of providing a blood test strip having a support member, a separating member and a recipient member. A quantity of blood is applied to the separating member which is greater than the combined absorptive capacities of the recipient and separating members. The blood is permitted to flow in the separating member. The cellular components of the blood are retained in the separating member.

One feature of the present invention is that the amount of plasma obtained and subjected to analysis is independent of the amount of blood applied to the strip, so long as the amount of blood applied is in excess of the combined absorptive capacities of the separating and recipient members. This feature has the advantage of obviating the need to dispense or apply a precise volume of blood on to the upstream end of the separating member.

Another feature of the present invention is that a blood test strip is provided which is compatible with both "wet" and "dry" chemical analysis procedures. This feature has the advantage of permitting the blood test strip to be used with a wide range of tests.

Additional features and advantages of the present invention will become apparent to those skilled in the art upon consideration of the following detailed description of the preferred embodiments exemplifying the best mode of carrying out the invention as presently perceived.

BRIEF DESCRIPTION OF THE DRAWINGS

FIG. 1 is a top-plan view of the test strip of the present invention;

FIG. 2 is a sectional view taken along line 2—2 of FIG. 1;

FIG. 3 is a top-plan view of a second embodiment of the present invention;

FIG. 4 is a sectional view taken along lines 4—4 of FIG. 3;

FIG. 5 is a top view of a third embodiment of the present invention;

DETAILED DESCRIPTION OF THE PREFERRED EMBODIMENTS

Figure 6:
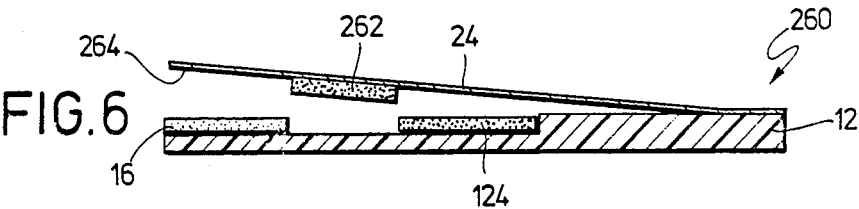
FIG. 6 is a side sectional view of a fourth embodiment of the present invention.

A blood test strip 10 is shown in FIGS. 1 and 2 as including a support member 12, a separating member 16, a recipient member 20, and a cover member 24.

The support member 12 includes an upper surface 28 and a lower surface 30. Although the lower surface 30 comprises a unitary plane, the upper surface 28 comprises two parallel plane portions, including a first, recessed portion 32 and a second portion 34, which serves as a handle for the blood test strip 10. The first portion 32 is recessed in order to permit the upper surfaces of the separating member 16 and recipient member 20 to be coplanar with the second portion 34. The support member 12 is made from a plastic material, such as polyvinyl or polystyrene, which is inert to the blood being tested and inert to reagents used in the analysis of the plasma separated by the blood test strip 10.

The support member 12 also includes a detachment means 36. The detachment means 36 preferably comprises a series of perforations, or a scoring of the support member 12. The perforations or scoring are positioned adjacent to the point where the separating member 16 and recipient member 20 meet, to facilitate the detachment of the separating member 16 from the remainder of the blood test strip 10 containing the recipient member 20. The removal of the separating member 16 helps to minimize interferences in the analytical procedures caused by the presence of the cellular components.

The separating member 16 is disposed on the first portion 32 of the support member 12, adjacent to the upstream end thereof, and consists of a three-dimensional network of glass or quartz fibers which are pressed together into a fleece. Such three-dimensional networks of glass or quartz fibers are typically referred to as a glass or quartz fiber paper. Fiber papers suitable for the separation of blood cells from plasma are now commercially available from several manufacturers such as Schleicher & Schuell, Whatman, Nuclepore and Gelman Sciences. Suitable papers generally have particle retentions between about 0.3 and 2.5 micrometers. Best results have been achieved with the Schleicher & Schuell glass fiber papers, Model Nos. 23 and 1-HV; Nuclepore glass fiber paper, Model No. P-300; Whatman EPM paper, and Whatman QM-A quartz fiber paper, although a slight hemolysis has been observed with the use of the Whatman EPM 200 and QM-A papers.

The separating member 16 of the embodiment shown in FIGS. 1 and 2 has an isosceles trapezoid shape, which helps to achieve a more efficient separation of the cells and plasma. As the cellular components and plasma flow from the upstream end 40 to the downstream end 42 of the separating member 16, the cellular components and plasma are continuously channeled from a wider to a narrower path of flow. In this way, the flow path of the cells is progressively compressed during the migration of the cells through the separating member 16, while the plasma component is pushed ahead. Through this compression of the blood cells, the distance increases between the "fronts" of the migrating plasma, and the migrating blood cells.

Attachment means are provided for attaching the separating member 16 to the support member 12. Although the separating member 16 can be glued to the support member 12, the use of a mechanical fastening means, such as spikes 44 is preferred. A method of attachment other than gluing is believed to facilitate the manufacturing process. Additionally, the chemicals used in glue can clog the fibers of the separating member 16, and can interfere with a chemical analysis performed on a sample contained on the strip 10. The spikes 44 can be formed on the support member 12 to extend upwardly therefrom, to pierce the underside surface of the separating member 16. This piercing prevents the separating member 16 from moving forwardly and laterally. The spikes 44 need not prevent upward movement of the separating member 16, as such upward movement would tend to be prevented by the cover member 24. Other methods of utilizing a fastening means include stapling, stitching, riveting or using a double-stick adhesive tape.

The recipient member 20 can be comprised of a variety of materials having varied chemical and physical characteristics. To a large extent, the choice of material used will depend on the particular test for which the device 10 is being used. The materials of choice for the recipient member 20 are typically hydrophilic polymers with a high absorptive capacity for plasma. Materials that can be used include chromatography paper, cellulose, cellulose nitrate, cellulose acetate, agarose and certain types of nylon. These materials are commercially available from companies such as Schleicher & Schuell, Whatman, Gelman, Nuclepore, Millipore, and Pall.

The recipient member 20 includes an upstream end 46 and a downstream end 48. The upstream end 46 is disposed adjacent to the separating member 16 in a side by side, non-interwoven relation to define a gap, or incision 50, therebetween. This incision 50 serves several beneficial purposes. Although the cells will pass through the incision 50 from the separating member 16 to the recipient member 20, the incision 50 helps to impede this flow somewhat. However, the presence of the incision 50 does not tend to impede the flow of plasma thereacross. Surprisingly, the plasma is transferred uniformly across the incision 50 from the separating member 16 to the recipient member 20. This uniformity of flow of the plasma occurs notwithstanding the differences in chemical and physical properties of the separating member 16 and the recipient member 20.

Another advantage achieved through the use of a discrete separating member 16 and a discrete recipient member 20 is that it permits the user to select a recipient member 20 having a desired absorptive capacity and size to allow the recipient member 20 to serve as a volumetric device for collecting a defined volume of the separated plasma. The volume of plasma subjected to analysis can thereby be controlled by varying the size (surface area) of the recipient member 20. Thus, discrete amounts of plasma can be obtained by properly selecting the size of a particular material used for the recipient member 20. Typically, this discrete amount of plasma collected is at least about 50% of the absorption volume of the separating member 16.

The collection of a defined volume of plasma on the recipient member 20 is achieved in the following manner: During the separation, the blood cells and plasma migrate away from the site of the blood application, with the plasma travelling ahead of the cell front. This separation is achieved as a result of combined capillary and filtration effects. When the recipient member 20 is filled (saturated) with plasma, additional blood will not be drawn into the recipient member 20, and the cell/plasma separating process comes to a halt. The size of the separating member 16 and recipient member 20 should be chosen so that at this saturation point, the blood cells are contained wholly, or at least predominantly, within the separating member 16. In this manner, the recipient member 20, (or a defined portion thereof), becomes a volumetric ("pipetting") device for the plasma separated. The ability of the recipient member 20 to serve as a volumetric device occurs so long as the amount of blood applied to the strip 10 is in excess of the combined absorptive capacities of the separating member 16 and the recipient member 20. As the recipient member 20 will serve as a volumetric device over a relatively broad range of blood amounts applied, the used need not apply a precise amount of blood to the separating member 16.

The cover member 24 is preferably comprised of a transparent plastic material for facilitating viewing of the cell/plasma separation process. For example, the cover member 24 can comprise a 0.010 inch thick strip of clear vinylite plastic. The size and shape of the cover member and the top surface of the blood test strip 10 are preferably identical. The end 54 of the cover member 24 is hingedly mounted to the supper surface 28 of the second portion 34, near the end thereof. This hinged mounting can be effected by either glue or a mechanical fastener, such as a staple, tack, stitch or spike. The cover member 24 serves a variety of functions. The cover member 24 helps to keep the separating and recipient members 16, 20 in their proper positions on spikes 44, and helps to protect the separating and recipient members 16, 20 from mechanical obstruction. In blood testing procedures performed on the recipient member 20, the transparency of the cover member 24 permits the user to monitor the test. Additionally, the cover member 24 helps to prevent evaporation of the separated plasma. Another advantage achieved through the use of cover member 24 helps to prevent evaporation of the separated plasma. Another advantage achieved through the use of cover member 24 is that the recipient member 20 can be attached to the cover member 24 to facilitate the removal of the recipient member 20, thereby increasing the range of tests with which the device 10 can be used, as will be explained in more detail below in connection with the embodiments shown in FIGS. 6-9.

An alternate embodiment blood test strip 110 is shown in FIGS. 3 and 4. Blood test strip 110 is similar in most respects to blood test strip 10 (shown in FIGS. 1 and 2), and identical numbers are utilized to designate identical parts of the two blood test strip embodiments 10, 110. The primary differences between blood test strip 110 and blood test strip 10 reside in the recipient member 120, the positioning of detachment means 136, and the provision of a second incision 150.

Blood test strip 110 includes a recipient member 120 which is comprised of a pair of recipient member segments, a first or transition recipient member segment 122, and a second or collection recipient member segment 124. The first recipient member segment 122 is disposed downstream from the separating member 16, and is placed in a side by side, non-interwoven relation thereto, to define an incision 50 therebetween. The transition zone provided by the first recipient member segment 122 is useful in some circumstances to provide an area for receiving any blood cells which may traverse incision 50. By serving as a repository for these traversing blood cells, the first recipient member segment 122 helps to ensure that the second recipient member segment 124 is generally devoid of such cells.

The second recipient member segment 124 is disposed adjacent to the downstream end of the first recipient member segment 122, and is placed in a side by side, non-interwoven relation to the first recipient member segment 122, to define a second incision 150 therebetween. The scoring or perforations which comprise the detachment means 136 are formed in the support member 12 directly below the second incision 150 in order to permit the separating member 16 and first recipient member segment 122 to be detached from the second recipient member segment 124, and the portion of the support member 12 coupled thereto. One advantage of having more than one recipient member segment is that plasma soluble chemical reagents can be incorporated into the first recipient member segment. Generally, such reagents would tend to be transferred by the separated plasma into the second recipient member segment. This storage of reagents in dry form on the test strip generally improves the chemical stability of the reagents. This is advantageous in situations where the test reaction employs one or more labile reagents.

Another alternate embodiment blood test strip 210 is shown in FIG. 5. Blood test strip 210 is generally similar to blood test strip 10 shown in FIGS. 1 and 2, except for the configuration of the separating member 216 of blood test strip 210. Separating member 216 comprises a generally widened, rectangular shaped separating member 216 which, when combined with the remainder of the test strip 210, gives the test strip a "T-shaped" configuration, with the separating member 216 being disposed along the head of the T and the recipient member 20 being disposed along the base of the T. This widened configuration of the separating member 216 functions somewhat similarly to the isosceles trapezoid shape of separating member 16, shown in FIGS. 1-4, in that it helps to channel the flow of plasma and red blood cells in a manner which enhances the separation of the plasma from the blood cells.

A fourth embodiment test strip 260 is shown in FIG. 6. Test strip 260 is generally similar to test strip 110 (shown in FIGS. 3 & 4), except that the first recipient member segment 262 of test strip 260 is attached to the underside surface 264 of cover member 24, rather than being attached to support member 12. Although FIG. 6 illustrates the cover member 24 in its raised position, during the time that blood is being applied to, and separated on the strip 260, the cover member 24 is placed in its lowered position, so that the first recipient member segment 262 is placed in a side by side, non-interwoven, coplanar relation to the separating member 16 and second recipient member segment 124. Through the placement of the first recipient member 262 on the underside surface 264 of the cover member 24, the plasma collected on the first recipient member segment 262 can be removed together with the hingedly attached cover member 24, and subjected to chemical analysis. In the embodiment shown in FIG. 6, the second recipient member 124 serves primarily as a reservoir for excess plasma.

One advantage of strip 260 is that an immobilized chemical reagent having a defined affinity for the substance to be measured can be incorporated into the first recipient member segment 262. As the plasma travels through the first recipient member segment 262, increasing amounts of the substance (in the plasma) to be measured are bound to the immobilized reagent, so that the plasma reaching the second recipient member segment 124 is relatively devoid of the substance to be measured. This relative accumulation or "trapping" of the substance to be measured in the first recipient member segment 262 may be advantageous in the analysis of substances that occur in the blood only in low concentrations. Examples of such substances include hormones and some components of the immune system.

Figure 7:
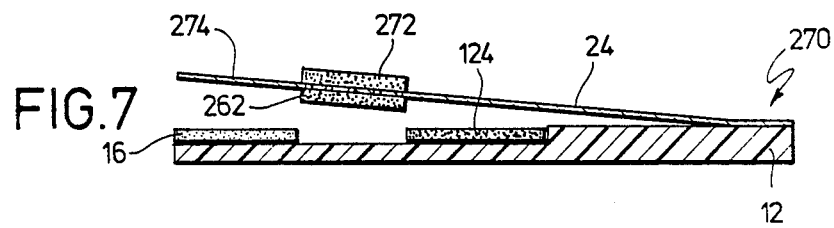
FIG. 7 is a side sectional view of a fifth embodiment of the present invention.

A fifth embodiment test strip 270 is shown in FIG. 7. Test strip 270 is generally similar to test strip 260 (shown in FIG. 6), except that test strip 270 includes a reagent pad 272 which is attached to the upper surface 274 of cover member 24, directly above the first recipient member segment 262. Depending on the type of test to be performed, the reagent pad 272 can be comprised of a paper or a hydrophilic membrane such as a cellulose acetate, cellulose nitrate, or nylon-66 membrane. The pad 272 is impregnated with one or more chemical reagents suitable to initiate a chemical reaction with a particular blood component. To carry out an analysis utilizing test strip 270, the cover member 24 is detached from the support member, and the part of cover member 24 which is disposed above separating member 16 is cut away from the remainder of the cover member 24. To elute the plasma components of the blood contained in the first recipient member segment 262, the cover member 24 is dipped into a small reaction vessel containing a small amount of a buffer or an augmenting reagent. If the reagent contained in the reagent pad 272 is diffusable, the color produced in the reaction vessel can be monitored. If the reagent in the reagent pad 272 is immobilized, the color can be read on the reagent pad 272. The test strip 270 shown in FIG. 7 permits labile reagents to be stored on the strip 270 in dry form, thus improving the stability of these reagents.

Figure 8:
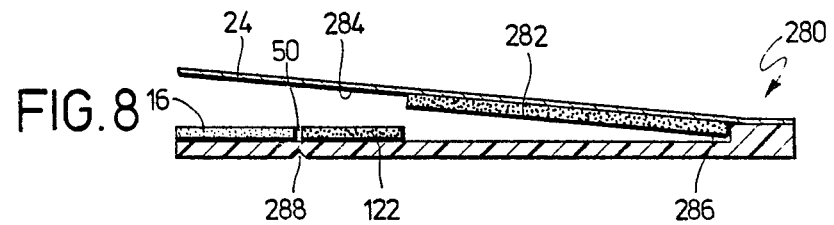
FIG. 8 is a side sectional view of a sixth embodiment of the present invention.

A sixth embodiment test strip 280 is shown in FIG. 8. Test strip 280 is generally similar to the test strip 110 shown in FIGS. 3 & 4, except that the second recipient member segment 282 is attached to the underside surface 284 of the cover member 24, and the scores or perforations which comprise the detachment means 288 are placed adjacent to the incision 50 between the separating member 16 and the first recipient member segment 122. With test strip 280, a defined volume of plasma can be collected on the first recipient member segment 122 while the cover member 24 (with the second recipient member segment 282 attached thereto) is placed in its raised position. Subsequent to the separation of the plasma, the separation member 16 can be detached from the support member 12, and the cover member 24 placed in its descended position so that the first and second recipient member segments 122, 282 are placed in a side-by-side, coplanar position.

Preferably, an immobilized reagent having a defined affinity to the substance to be measured is incorporated into the second recipient member segment 282. The plasma can then be eluted from the first recipient member segment 122 into the second recipient member segment 282 with a buffer or an augmenting reagent. This causes the substance to be measured to travel toward the downstream end 286 of the second recipient member segment 282. At an appropriate concentration ratio of the substance to be measured and the immobilized reagent contained in the second recipient member segment 282, one can measure the concentration of the substance by the distance that the substance travels toward the downstream end 286 of the second recipient member segment 282.

Figure 9:
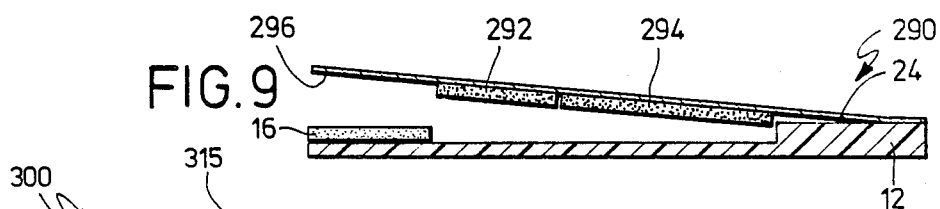
FIG. 9 is a side sectional view of a seventh embodiment of the present invention.

A seventh embodiment test strip 290 is shown in FIG. 9. Test strip 290 is generally similar to test strip 280 (shown in FIG. 8), except that both the first and second recipient member segments 292, 294 are attached to the underside surface 296 of the cover member 24 in a side-by-side, non-interwoven relation. In contrast to the manner in which test strip 280 is used, the cover member 24 of test strip 290 is placed in its descended position at the time that the blood is applied to the separating member 16. Preferably, an immobilized reagent is contained in the first recipient member segment 292. The immobilized reagent performs the function of trapping the substance to be analyzed as it is transported across the first recipient member segment 292 by the separated plasma. The second recipient member segment 294 is provided for collecting excess plasma.

After the plasma has been separated, the cover member 24 is lifted and the detection reaction is initiated by adding the auxiliary reagents to the first recipient member segment 292. One advantage obtained by the use of test strip 290 is that it readily permits the removal of all the plasma components not subject to analysis. This removal takes place by flushing these plasma components into the second recipient member segment 294, and can be effected either with a wash solution or an augmenting reagent. Thus, the second recipient member segment 294 becomes a reservoir for excess plasma and any fluid applied during the test to the first recipient member segment 292. In this way, the device allows both the removal of plasma components that may otherwise interfere with the test, and the removal of excess reagents and wash solutions by absorbing them into the second recipient member segment 294. The device permits this removal to take place directly on the test strip 290. Another advantage of test strip 290 is that the detachment of the separating member 16 prior to the performance of a test is facilitated, as the user can detach the recipient member segments 292, 294 from the separating member 16 by detaching the cover member 24 containing the recipient member segments 292, 294.

Figure 10:
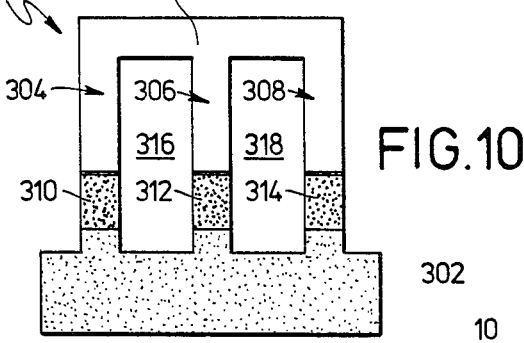
FIG. 10 is a top view of an eighth embodiment of the present invention.

A test strip 300 on which a plurality of tests can be conducted simultaneously is shown in FIG. 10. Test strip 300 includes a unitary separating member 302 which extends across the entire width of the test strip 300, forming a bottom leg thereof. The test strip 300 also includes first, second and third upstanding legs 304, 306, 308, on which are disposed first, second and third recipient members 310, 312, 314, respectively. A top leg 315 connects the three upstanding legs 304, 306, 308, and defines first and second cut-out portions 316, 318, formed between the three upstanding legs 304, 306, 308. One advantage of the use of the test strip 300 shown in FIG. 10 is that it can be used for the analysis of a panel or profile of blood constituents, wherein different reagents exerting different chemical affinities to these constituents are contained in, or applied to the different recipient members 310, 312, 314.

Figure 11:
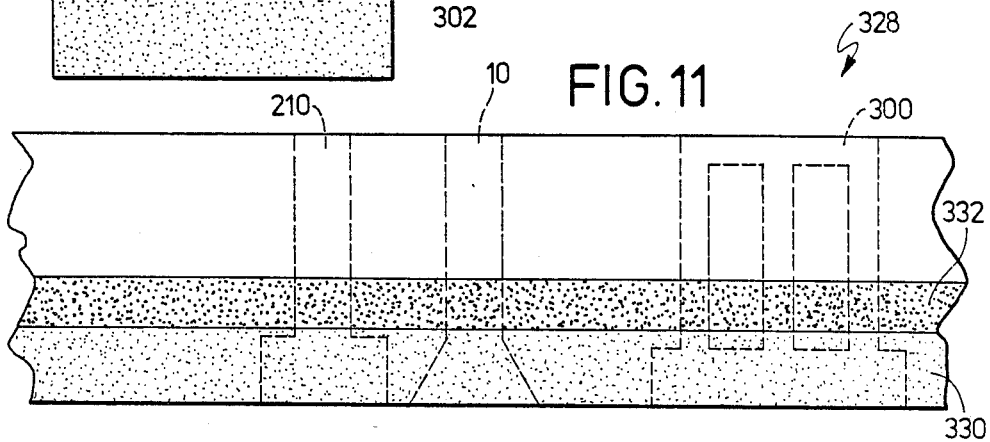
FIG. 11 is a top view of a template from which the test strips can be produced.

A continuous strip 328 from which the various test strips can be cut is shown in FIG. 11. Continuous strip 328 includes a continuous strip of separating material 330 and a continuous strip of recipient member material 332. The various individual test strips, e.g. test strips 10, 210 or 300, are preferably die cut from this continuous strip. In the manufacture of test strips, such as test strip 110, which include two recipient member segments disposed in a side-by-side, non-interwoven relation, it will be appreciated that the recipient member material strip 332 would comprise two appropriately sized recipient member material strips disposed in a non-interwoven, side-by-side relationship.

The method by which blood is applied to the upstream end of the separating member of the above discussed strips can be varied to best accommodate the requirements of a particular test. For example, if only a small volume of plasma is required, the separating member may be held directly onto a blood droplet from a finger prick, to allow the blood to enter onto the upstream end of the separating member and then flow downstream into the separating member. As will be appreciated, the plasma would then cross the incision and progressively saturate the recipient member.

Figure 12:
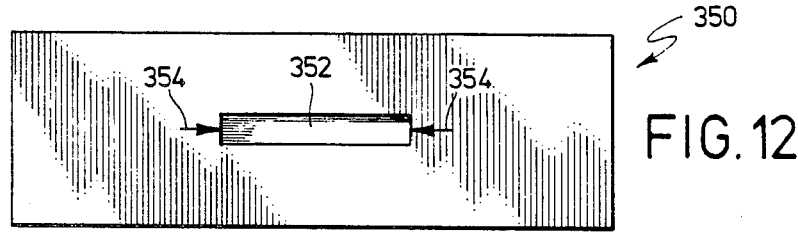
FIG. 12 is a top view of a blood reservoir for the present invention.
Figure 13:
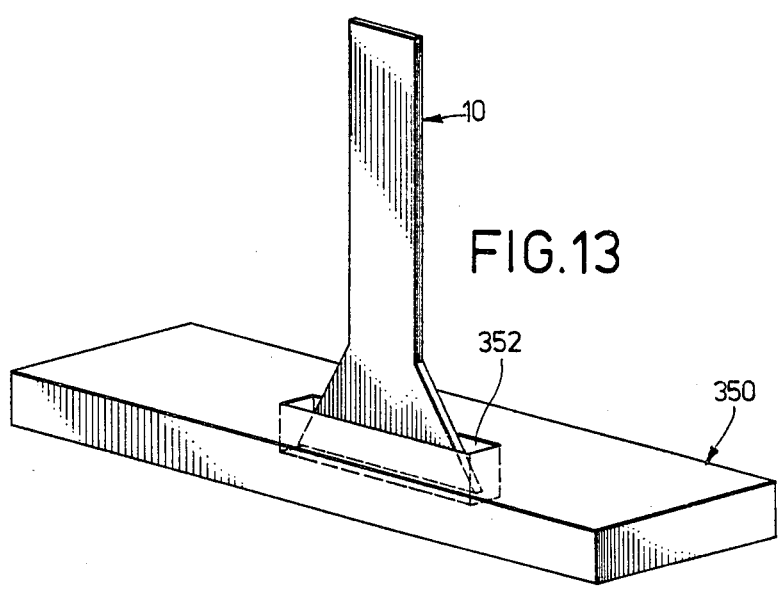
FIG. 13 is a perspective view of a test strip being utilized with the blood reservoir.

If larger volumes of plasma are required, the blood may first be collected in a receptacle such as receptacle 350 shown in FIGS. 12 & 13. Receptacle 350 preferably comprises a small plastic plate having a reservoir 352 contained therein. The reservoir 352 has a volume great enough to hold a sufficient amount of blood, and a width 354 great enough to accomodate the upstream end of a test strip, e.g., test strip 10. The upstream end of the test strip 10 is inserted into the opening (as shown in FIG. 13) and blood is allowed to ascend in the strip. As the blood ascends in the strip, the cellular components of the blood are held within the separating member, while the plasma component is collected on the recipient member.

As will be appreciated, the test strips of the present invention can be used in a wide range of diagnostic applications. The test strips of the present invention are universally applicable to both "wet" and "dry" types of chemical analysis. This universality is possible because subsequent to separation, the plasma so separated can be brought into contact with liquid reagents or reagents contained in dry reagent carrier materials.

The most basic "wet" application of the present invention is to use the test strip to separate plasma, and then to bring the separated plasma into contact with a liquid reagent. The progress of the reaction is monitored, either photometrically or visually, depending on whether a quantitative, semi-quantitative, or qualitative result is needed.

Alternately, in a "dry" application, a blotting type technique can be used, whereby the separated plasma is brought into contract with a reagent contained in a dry reagent carrier.

Finally, dry reagents can be incorporated into the separating and/or recipient members or in an additional reagent pad attached to the strip. In these types of applications, the reaction is initiated either by the dry reagent (as is) on the strip or by exposing the strip to augmenting reagents. Presented below are selected potential applications of the device:

The embodiments 10, 110, 210, and 260, which are shown in FIGS. 1-6, respectively, are suitable for applications wherein the primary purpose served by the device is to separate a defined volume of plasma for analysis. By exposing the recipient member, or a recipient member segment to a specific liquid reagent, essentially all constituents occurring in blood can be analyzed through the use of an appropriate reagent. These reagents are now available in various configurations from a variety of diagnostic manufacturers.

Similar applications are possible with the embodiment shown in FIG. 7, wherein the cover member 24 carrying the separated plasma, and one or more dry reagents contained in the reagent pad 272 are inserted into a reaction vessel (not shown) containing a buffer or augmenting reagent(s). One example of such a test is an enzymic procedure for the testing of blood cholesterol, wherein the reagent pad contains the components cholesterol esterase, cholesterol oxidase, peroxidase and a leuko dye. Upon insertion of the cover member 24 containing the reagent pad 272 and first recipient member segment 262, into the reaction buffer, the plasma and reagents are eluted together, and the enzymic reaction sequence is allowed to proceed.

The test strips 260, 290 illustrated in FIGS. 6 and 9, respectively, are suitable for qualitative and semi-quantitative immunoassays. In tests wherein the objective is to detect plasma antibodies to certain disease antigens, the antigenic materials can be immobilized into the respective first recipient member segments 262, 292. As the plasma passes through these first recipient member segments 262, 292, the formation of antigen-antibody complexes occurs. The amount of antibody retained in the first recipient member segments 262, 292 is a function of the antibody concentration in the plasma, the density of antigen packing within the recipient member, and the amount of plasma allowed to flow laterally through the first recipient member segments 262, 292. Accordingly, the sensitivity of the assays can be modulated by varying the antigen concentration and plasma flow through the first recipient member segments 262, 292. Typically, the immuno-sandwich is completed by reacting the primary complex with an enzyme labeled second antibody. After the removal of excess unbound second antibody, the reaction of antibody bound enzyme with a suitable substrate would indicate the presence or concentration of primary antibody.

A variety of teachings exist which are applicable to these assay technologies. Antibodies assayable by this type of assay procedure include the antibody (HTLV III) associated with acquired immune deficiency syndrome (AIDS), antibodies associated with hepatitis, chlamydia trachomatis, as well as many others.

Similarly, serum antigens are assayable by these same devices if the antigen's corresponding antibodies are immobilized within the recipient member. For example, double antibody assays could be designed for human chorionic gonadotrophin (HCG, pregnancy) or the MB subunit of creatine kinase, whereby the two antibodies react with specific antigenic determinants located on different sub-units, or with two different antigenic sites located within one antigen molecule. Extensive prior art exists teaching these assay principles.

In some applications, it may be desirable to determine the presence of more than one blood constituent in a single analytic procedure. For such panel or profile type testing, the embodiment shown in FIG. 10 is suitable. Examples of such panel type testing include specific IgE allergen antibodies, an antibody panel for toxoplasmosis, rubella, cytomegalovirus and herpes (TORCH) or a drug panel.

The embodiment 280 shown in FIG. 8 is useful for quantitative immunodiffusion or immunochromatographic type assays not requiring instruments. Single direction immunodiffusion is feasible for serum proteins of higher concentrations, such as immunoglobulins, complement or apolipoproteins. In these applications, a defined volume of plasma is collected on the first recipient member segment 122 with the cover member 24 in the lifted or raised position. Preferably, the second recipient member segment 282 comprises a bed of agarose containing an immobilized antibody specific to the analyte to be measured. Subsequent to the plasma separation, the separating member 16 is detached and the cover member 24 placed in its descended position. The plasma is diffused into the second recipient member segment 282 by applying a small quantity of buffer. Upon completion of immunodiffusion, the precipitin lines formed indicate respective zones of analyte/antibody equivalence.

In a related application, the substance to be measured could be a therapeutic drug of a drug of abuse. In this case, the second recipient member 282 would contain an immobilized antibody to the drug, and the first recipient member segment 122 would be impregnated with a mobile enzyme conjugate of the drug. After plasma separation, the first recipient member segment 122 contains a mixture of the drug conjugate and the analyte drug from the patient's blood sample. As the mixture is chromatographed into the second recipient member segment 282, the enzyme conjugate of the drug competes with the free drug for the binding sites on the antibody. The greater the quantity of free drug that is contained in the patient's plasma, the greater the quantity of enzyme labeled drug that is displaced from the antibody binding sites. As a result of this displacement, the enzyme labeled drug travels further downstream on the second recipient member segment 282 until antigen-/antibody equivalence is reached.

An assay of this type has recently been introduced by the Syva Company of Palo Alto, California and is marketed under the Trademark ACCULEVEL. In this product, the enzyme peroxidase is conjugated with the drug of interest. Free drug from the patient serum and drug conjugate compete for the antibodies which are immobilized on a strip of chromatography paper. The indicator reagent contains glucose, glucose oxidase and a leuko dye. In the detection reaction, glucose oxidation and stoichiometric hydrogen peroxide generation occur everywhere on the strip, but dye conversion takes place only on the drug-peroxidase containing portion of the strip. As the distance of the front of the drug-peroxidase containing portion from the upstream end of the strip 280 is related to the free drug concentration, the length of the colored zone becomes a measure of drug concentration.

Although the above description of the present invention is directed primarily to the use of the device to separate blood components, it will be appreciated by those skilled in the are that the device would have utility in the separation of cellular components of other body fluids such as urine, spinal fluid, and others.

Having described the invention in detail, and by reference to the preferred embodiments thereof, it will be apparent that modifications and variations are possible without departing from the scope of the invention defined in the appended claims.

What is claimed is:

1. A blood test strip comprising:
   a support member having an upper surface and a lower surface,
   a sheet-like separating member disposed on the upper surface of the support member for separating blood cells from plasma, the separating member including an upstream end and a downstream end,
   a sheet-like recipient member disposed on the upper surface of said support member in a generally coplanar, side-by-side relation with the separating member, the recipient member including an upstream end disposed in an adjacent, non-interwoven relation to the downstream end of the separating member to define an incision therebetween.

2. The invention of claim 1 wherein said recipient member comprises at least two sheet-like recipient member segments disposed adjacent to each other in a generally co-planar, side-by-side, non-interwoven relation to define an incision therebetween.

3. The invention of claim 2 wherein the support member includes a detachment means disposed adjacent to at least one of said incisions for permitting at least one of said recipient member segments to be detached from said separating member.

4. The invention of claim 1 wherein said upstream end of said separating member is generally wider than said downstream end of said separating member.

5. The invention of claim 1 wherein said separating member has a generally isosceles trapezoid shape, the upstream end of said separating member being wider than the downstream end of the separating member.

6. The invention of claim 1 wherein said separating member is wider than the recipient member to impart a T-shape to said blood test strip.

7. The invention of claim 1 further comprising mechanical fastener means for fastening the separating member and recipient member to the support member.

8. The invention of claim 7 wherein said mechanical fastener means comprises staples.

9. The invention of claim 7 wherein said mechanical fastener means comprises thread.

10. The invention of claim 7 wherein said mechanical fastener means comprises spikes.

11. The invention of claim 7 wherein said mechanical fastener means comprises double stick tape.

12. The invention of claim 1 wherein said recipient member comprises a hydrophilic polymer having a defined absorptive capacity.

13. The invention of claim 1 further comprising a cover member hingedly attached to the support member to overlay the recipient member and the separating member.

14. The invention of claim 13 wherein said cover member includes a top surface and a bottom surface, and said recipient member is disposed on the bottom surface, further comprising a reagent pad disposed on said top surface directly above said recipient member, the reagent pad being in fluid communication with said recipient member.

15. The invention of claim 14 wherein said reagent pad is impregnated with a chemical reagent for initiating a reaction with a blood component collected on said recipient member.

16. A test strip for separating components of a body fluid comprising:
    a support member having an upper surface and a lower surface,
    a generally sheet-like separating member including an upstream end and a downstream end,
    a generally sheet-like recipient member including an upstream end and a downstream end, and a cover member attached by hinges to the support member for overlaying the support member, the cover member including an underside surface, one of said separating member and recipient member being attached to said upper surface of said support member and the other of said separating member and recipient member being attached to said underside surface of said cover member, the member attached to the support member and the member attached to the cover member being cooperatively positioned to be placeable in a generally co-planar, side-by-side, non-interwoven relation to define an incision therebetween.

17. The invention of claim 16 wherein said recipient member comprises first and second recipient member segments.

18. The invention of claim 17 wherein one of said first and second recipient member segments is attached to said cover member, and the other of said first and second recipient member segments is attached to said support member.

19. The invention of claim 17 wherein both said first and second recipient member segments are attached to said cover member.

20. A method for separating plasma from whole blood comprising:
   providing a blood test strip including
   (1) a support member,
   (2) a generally sheet-like separating member, and
   (3) a generally sheet-like recipient member, the recipient member being disposed in a generally co-planar, side-by-side, non-interwoven relation with the separating member to define an incision therebetween, the recipient member having a defined absorptive capacity,
   applying a quantity of blood to the separating member in excess of the combined absorptive capacities of the separating member and recipient member,
   permitting the blood to flow in the separating and recipient members,
   collecting a defined volume of plasma on the recipient member, and
   retaining the cellular components of the blood in the separating member.

21. The method of claim 20 wherein the step of providing a recipient member comprises the step of providing a recipient member comprised of at least two recipient member segments disposed adjacent to each other in a side by side, non-interwoven relation to define an incision therebetween, one of said at least two recipient member segments having said defined absorptive capacity.

22. A method for separating plasma from whole blood comprising:
   providing a blood test strip including:
   (1) a support member,
   (2) a separating member, and
   (3) a recipient member comprising at least two recipient member segments disposed in a side-by-side, non-interwoven relation to define an incision therebetween, one of said at least two recipient member segments having a defined absorptive capacity,
   applying a quantity of blood to the separating member in excess of the combined absorptive capacities of the separating member and the recipient member,
   permitting the blood to flow in the separating and recipient members,
   collecting a defined volume of plasma on the recipient member,
   retaining the cellular components of the blood in the separating member,
   detaching said recipient member segment having a defined absorptive capacity from said strip, and
   utilizing the plasma collected thereon in a blood test procedure.

23. A blood test trip comprising:
   a support member having an upper surface and a lower surface,
   a separating member disposed on the supper surface of the support member, the separating member including an upstream end and a downstream end,
   a recipient member disposed on the upper surface of the support member in a side-by-side relation with the separating member, the recipient member including an upstream end disposed in an adjacent, non-interwoven relation to the downstream end of the separating member to define an incision therebetween, and
   a detachment means disposed adjacent to the incision for permitting the recipient member to be detached from said separating member.

24. The invention of claim 23 wherein said recipient member comprises at least two recipient member segments disposed adjacent to each other in a side-by-side, non-interwoven relation to define an incision therebetween, and
   said detachment means is disposed on the support member for permitting at least one of said recipient member segments to be detached from said separating member.

25. A method for separating plasma from whole blood comprising:
   providing a blood test strip including a recipient member having a defined absorptive capacity, and a separating member, the recipient member and separating member being disposed in a generally co-planar, side by side relation,
   applying a quantity of blood to the separating member in excess of the combined absorptive capacities of the separating member and the recipient member,
   permitting the blood to flow in the separating member and recipient member,
   collecting a defined volume of plasma on the recipient member,
   retaining the cellular components of the blood in the separating member,
   detaching the recipient member from the blood test strip, and
   utilizing the plasma collected in a blood test procedure.

* * * * *